US008303989B2

(12) United States Patent
Choi et al.

(10) Patent No.: US 8,303,989 B2
(45) Date of Patent: Nov. 6, 2012

(54) COMPOSITIONS AND METHODS FOR INCREASING THE ORAL ABSORPTION OF ANTIMICROBIALS (75) Inventors: Seung-Ho Choi, Salt Lake City, UT (US); Jeoung-Soo Lee, Salt Lake City, UT (US); Dennis Keith, Montclair, NJ (US)

(73) Assignee: International Health Management Associates, Inc.

( * ) Notice: Subject to any disclaimer, the term of this patent is extended or adjusted under 35 U.S.C. 154(b) by 0 days.

(21) Appl. No.: 12/425,099

(22) Filed: Apr. 16, 2009

(65) Prior Publication Data

US 2009/0264340 A1  Oct. 22, 2009

Related U.S. Application Data (63) Continuation of application No. 09/888,114, filed on Jun. 22, 2001, now Pat. No. 7,527,807, which is a continuation-in-part of application No. 09/829,405, filed on Apr. 9, 2001, now abandoned, which is a continuation of application No. 09/598,089, filed on Jun. 21, 2000, now Pat. No. 6,248,360, said application No. 09/888,114 is a continuation of application No. PCT/US01/19625, filed on Jun. 18, 2001.

(60) Provisional application No. 60/283,976, filed on Apr. 16, 2001.

(51) Int. Cl.
*A61K 9/62* (2006.01)

(52) U.S. Cl. ........ 424/488; 424/484; 514/9; 514/210.05; 514/777; 514/785

(58) Field of Classification Search .................. None
See application file for complete search history.

(56) References Cited

U.S. PATENT DOCUMENTS

| | | |
|---|---|---|
| 3,725,400 A | 4/1973 | Voser |
| 3,886,125 A | 5/1975 | Chromecek |
| 4,188,373 A | 2/1980 | Krezanoski |
| 4,525,339 A | 6/1985 | Behl et al. |
| 4,574,152 A | 3/1986 | Noble |
| 4,616,008 A | 10/1986 | Hirai et al. |
| 4,732,753 A | 3/1988 | Füller |
| 4,902,501 A | 2/1990 | Bandi et al. |
| 5,260,292 A | 11/1993 | Robinson et al. |
| 5,318,781 A | 6/1994 | Shah et al. |
| 5,472,704 A | 12/1995 | Santus et al. |
| 5,726,154 A * | 3/1998 | Baudys et al. ............... 514/12 |
| 5,783,561 A | 7/1998 | Horwitz et al. |
| 5,852,004 A | 12/1998 | Barritault et al. |
| 5,856,474 A | 1/1999 | Ascher et al. |
| 5,861,508 A | 1/1999 | Ludescher et al. |
| 5,968,253 A | 10/1999 | Poser et al. |
| 5,968,895 A | 10/1999 | Gefter et al. |
| 5,994,340 A | 11/1999 | Maiti et al. |
| 6,004,583 A * | 12/1999 | Plate et al. ............... 424/486 |
| 6,017,513 A | 1/2000 | Betbeder et al. |
| 6,025,352 A | 2/2000 | Cho et al. |
| 6,063,917 A | 5/2000 | Ascher et al. |
| 6,071,447 A | 6/2000 | Bootman et al. |
| 6,093,813 A | 7/2000 | Ascher et al. |
| 6,214,378 B1 | 4/2001 | Tanida et al. |
| 6,232,306 B1 | 5/2001 | Hebeisen et al. |
| 6,248,360 B1 | 6/2001 | Choi et al. |
| 6,315,981 B1 | 11/2001 | Unger |
| 6,458,387 B1 | 10/2002 | Scott et al. |
| 6,458,772 B1 | 10/2002 | Zhou et al. |
| 6,465,626 B1 | 10/2002 | Watts et al. |
| 6,727,243 B1 | 4/2004 | Jennewein et al. |
| 6,902,743 B1 | 6/2005 | Setterstrom et al. |
| 7,527,807 B2 * | 5/2009 | Choi et al. ............... 424/488 |
| 2002/0004499 A1 | 1/2002 | Rudnic et al. |
| 2002/0051820 A1 | 5/2002 | Shell et al. |
| 2002/0119195 A1 | 8/2002 | Sen et al. |
| 2004/0131665 A1 | 7/2004 | Wepfer |
| 2004/0208936 A1 | 10/2004 | Chorin et al. |
| 2005/0020537 A1 | 1/2005 | Leung et al. |
| 2005/0037071 A1 | 2/2005 | Cao et al. |

FOREIGN PATENT DOCUMENTS

| | | |
|---|---|---|
| EP | 0 207 624 B1 | 1/1987 |
| EP | 0 213 552 | 3/1987 |
| EP | 0 526 862 B1 | 2/1993 |
| EP | 0 580 428 B2 | 1/1994 |
| JP | 60-67413 | 4/1985 |
| JP | 1999-92402 | 6/1999 |
| JP | 2000-302621 | 10/2000 |
| WO | 9620698 | 7/1996 |
| WO | 9830207 | 7/1998 |
| WO | WO 99/31106 | 6/1999 |
| WO | 99/49868 | 10/1999 |
| WO | 9949868 A1 | 10/1999 |
| WO | 01/01959 | 1/2001 |
| WO | 01/32218 | 5/2001 |
| WO | 01/97851 | 12/2001 |
| WO | 02/04012 | 1/2002 |
| WO | 2004/066976 | 8/2004 |
| WO | 2004/073695 | 9/2004 |
| WO | 2005/018618 | 3/2005 |

OTHER PUBLICATIONS

Definition "biopolymer", The On-line Medical Dictionary, cancerweb.ncl.ac.uk/omd/ (Feb. 2006).

(Continued)

*Primary Examiner* — Neil Levy (74) *Attorney, Agent, or Firm* — Lando & Anastasi LLP (57) ABSTRACT

The present invention provides compositions and methods for increasing absorption of antibacterial agents, particularly third generation cephalosporin antibacterial agents, in oral dosage solid and/or suspension forms. Specifically, the composition is comprised of a biopolymer that is preferably swellable and/or mucoadhesive, a antimicrobial agent, and a cationic binding agent contained within the biopolymer such that the binding agent is ionically bound or complexed to at least one member selected from the group consisting of the biopolymer and the antimicrobial agent.

1 Claim, 4 Drawing Sheets

OTHER PUBLICATIONS

Bretschneider et al., "Intestinal Transport of β-Lactam Antibiotics: Analysis of the Affinity at the H$^+$/Peptide Symporter (PEPT1), the Uptake into Caco-2 Cell Monolayers and the Transepithelial Flux", *Pharm. Res.* 16(1):55-61 (1999).

Choi, Tenth International Symposium on Recent Advances in Drug Delivery Systems, Feb. 19-22, 2001.

Goldstein et al., "Comparative in Vitro Activities of Ertapenem (MK-0826) against 1,001 Anaerobes Isolated from Human Intra-Abdominal Infections", *Antimicrob. Agents Chemother.* 44(9):2389-2394 (2000).

Imamura et al., "Stereoselective Synthesis of a Broad Spectrum 1β-Methylcarbapenem, J-114,870", *Tetrahedron* 56:7705-7713 (2000).

Jiraskova, "RWJ-333441 Microcide/RW Johnson", *Curr Opin Invest Drugs* 2(2):209-211 (2001).

Lee et al., "Bioadhesive-Based Dosage Forms: The Next Generation", *J. Pharm. Sci.* 89(7):850-866 (2000).

Longer et al., "Bioadhesive Polymers as Platforms for Oral Controlled Drug Delivery III: Oral Delivery of Chlorothiazide Using a Bioadhesive Polymer", *J. Pharm. Sci.* 74(4):406-411 (1985).

Natsume et al., "Screening of cationic compounds as an absorption enhancer for nasal drug delivery", *Int. J. Pharm.* 185:1-12 (1999).

Sorbera et al., "MK-0826", *Drugs of the Future* 25(8):795-802 (2000).

van Ogtrop, "MK-826 Merck & Co", *Curr. Opin Anti-Infect. Invest. Drugs* 1(1):74-77 (1999).

Cho et al., "Enhanced oral bioavailability of poorly absorbed drugs. I. Screening of absorption carrier for the ceftriaxone complex," Journal of Pharmaceutical Sciences, 93(3):612-620 (2004).

Kato et al., "Lack of interaction between cefdinir and calcium polycarbophil: In vitro and in vivo studies," Drug Metabolism and Pharmacokinetics, 17(4):363-366 (2002).

Wikipedia excerpt for "Cephalosporine".

Ueda et al. "Effect of Ethyl Cellulose in a Medium-Chain Triglyceride on the Bioavailability of Ceftizoxime", J. Pharm. Sci. 1983, 72 (4), pp. 454-458.

Excerpt of RÖmpp's chemical dictionary (RÖmpp's Lexikon Chemie, 10th Ed., 1997, p. 445).

Third party observations from European Application Serial No. 01944619.4 dated Jul. 9, 2010.

Rote Lisle, 1999.

* cited by examiner

FIGURE 1

Intraduodenal Dosing in Monkeys
20 mg/kg OCTX1 + Capmul

Intraduodenal Dosing in Rats
40 mg/kg OCTX1 + Capmul

COMPOSITIONS AND METHODS FOR INCREASING THE ORAL ABSORPTION OF ANTIMICROBIALS

This application is a continuation of and claims priority to U.S. Ser. No. 09/888,114 filed Jun. 22, 2001, now U.S. Pat. No. 7,527,807, which is a continuation-in-part of U.S. Ser. No. 09/829,405, filed Apr. 9, 2001, now abandoned, which is a continuation of U.S. Ser. No. 09/598,089, filed Jun. 21, 2000, now U.S. Pat. No. 6,248,360. U.S. Ser. No. 09/888,114 is also a continuation of International PCT Serial No. PCT/US01/19625, filed Jun. 18, 2001 (published in English), and claims the benefit of a previously filed Provisional Application No. 60/283,976, filed Apr. 16, 2001. The contents of these application are incorporated herein by reference.

FIELD OF THE INVENTION

The present invention is related to compositions and methods for improving the intestinal absorption of antimicrobial agents and their pharmaceutically acceptable salts, esters, ethers or hydrates by combining the selected antimicrobial agent with a cationic binding agent and a biopolymer, and, optionally, an absorption enhancer. Particularly the invention is related to compositions and methods for improving the intestinal absorption of third generation cephalosporin antimicrobial agents, carbapenem and lipopeptide antibacterial agents.

BACKGROUND OF THE INVENTION

The gastrointestinal tract, ("GI") particularly the small intestines, is the primary site for the absorption of nutrients and most bioactive agents. To accommodate the amount of absorption that must take place in the small intestines, the surface area is enlarged due to the presence of villi and microvilli. However, before a bioactive compound is transferred from the intestinal lumen to the blood, the compound may have to withstand degradation or deactivation by the various components of the luminal contents. Moreover, the compound may be required to pass through several absorption barriers, such as the mucous layer and the intestinal brush-border membrane. Many compounds pass these barriers easily, but there are many nutrients and bioactive agents to which these barriers represent a serious obstruction.

There are many contributing factors which can affect the oral bioavailability of drugs in the gastrointestinal tract. They include for example, characteristics of the GI tract itself, such as the thickness of the epithelium, the surface area, and blood flow, as well as the local physical and chemical environment. Additionally, absorption may be affected by characteristics of the drug substance itself, such as its solubility in water, its chemical stability and molecular weight.

Cephalosporin is the general term for a group of antibiotic derivatives of cephalosporin C, which is obtained from the fungus *Cephalsporium Acremonium*. First generation cephalosporins and most second generation cephalosporins are functional in oral dosage forms, though they may be ineffective against many forms of bacteria, such as those found in typical hospital infections. Many third generation cephalosporins, such as ceftiofur, cefixime, cefepime, cefoperazone, cefotaxime, cefpodoxime, ceftazidime, ceftizoxime and ceftriaxone, due to their broad spectrum of activity, are effective against some bacterial strains that are resistant to many first and second generation cephalosporins. However, since they are generally not orally bioavailable they must be given by injection. There are several contributing factors to the low absorption in the intestines of third generation cephalosporins after oral administration. First, these antibacterial agents are generally highly ionized and hence are very polar and hydrophillic. These properties do not allow them to readily penetrate the hydrophobic intestinal mucosal membrane. Second, due to their reactive properties, these antibacterial agents are generally unstable in an aqueous environment such as in gastric juices and small intestinal fluids.

Therefore, these cephalosporins have been less effective when administered by other than parenteral routes to treat systemic bacterial infections. Frequently these agents must be given more than once daily to achieve the desired level of efficacy. The necessity of obtaining treatment through intravenous (i.v.) or intramuscular (i.m.) injections is inconvenient, as such treatments often require the services of doctors, nurses, or other trained technicians. Additionally, injections can be painful and cause undue physical and psychological stress to many patients, especially to pediatric patients.

Although ionic surfactants, such as sodium lauryl sulfate, or chelating agents such as EDTA, have been found in some cases to enhance intestinal absorption of large molecules, these substances are known to be harmful to the mucosal membrane.

Other technologies have shown some promise in providing compositions and methods for delivering third generation cephalosporins orally through increased intestinal absorption. In U.S. Pat. No. 4,525,339, β-lactam antibacterial agents were shown to penetrate the mucosal membrane of the intestines by co-administering $C_2$-$C_{12}$ fatty acid mono-, di-, or triglycerides (i.e. such as Capmuls) as absorption enhancers. In U.S. Pat. No. 5,190,748, absorption of antibacterial agents (such as ceftriaxone) through oral and rectal routes was enhanced by utilizing a two-component absorption enhancing system comprising an ether of a $C_6$-$C_{18}$ alcohol and a polyoxyethylene glycol together with a second component selected from the group consisting of polyoxyethylene glycol $C_6$ to $C_{18}$ glyceride esters, $C_6$ to $C_{18}$ carboxylic acids or salts thereof, and esters of two or more $C_6$ to $C_{18}$ carboxylic acids, glycerol, and a polyoxyethylene glycol. Additionally, in U.S. Pat. No. 5,318,781, absorption of antibacterial agents (such as ceftriaxone) through oral and rectal routes was enhanced by utilizing a two-component absorption enhancing system comprising Laureth-12 and a second component salt of capric acid and caprylic acids, and a carrier. For optimum absorption, the antimicrobial agent containing the two component enhancer system disclosed therein may include Miglyol-812, which is a capryllic/capric triglyceride. In U.S. Pat. No. 4,722,941, the permucosal absorption of various therapeutics, including antibacterial agents, is reported to be enhanced by the use of fatty acids and saturated or unsaturated fatty acid glycerides.

Other disclosures related to improvements in the intestinal delivery of antibiotics include, for example, oral preparations combining a polymer which is soluble only at pH 5.5 or higher and an insoluble polymer targeted for release in the large intestine (European Patent 49,590); and a solid oral dosage form coated with an appropriate amount of anionic polymer WO 83/00435).

Although each of these systems are somewhat effective in delivering antibacterial agents through the mucosal membrane after oral delivery, each has drawbacks that prevent their widespread use. Some of the compositions and/or methods do not provide significant enough drug delivery such that functional use is practical. Additionally, other compositions and/or methods of mucosal delivery are too costly. As the benefits of third generation cephalosporins and other antibacterial agents have become apparent, it is desirable to provide compositions and methods for administering these antibacterial agents orally, and thus, provide an administration route that is more convenient and cost effective to the patient, and enhances functional concentration of antimicrobial agent that may be absorbed.

Low absorption of oral antimicrobial agents is detrimental for a variety of reasons. Efficacy of the drug may be reduced or eliminated due to the low amounts of drug crossing from the GI tract into the systemic circulation. Safety and tolerability may be compromised since a large amount of the drug ingested may end up in the colon, causing diarrhea, colitis and other gastrointestinal problems. As a result, there may be an increased incidence of drug resistant organisms "selected" in the colon due to the higher levels of drug present.

The present invention addresses the need for orally bioavailable antimicrobial agents by providing compositions and methods for improving the absorption of antimicrobial agents that overcome the difficulties associated with the methods and compositions known in the art.

SUMMARY OF THE INVENTION

The present invention discloses compositions and methods useful for the multitude of therapeutic classes of drugs where lack of transport across the intestinal mucosa limits the systemic uptake of active drug ingredients, or where increased systemic uptake is desired. Such therapeutic classes of drugs include, for example, all antimicrobial agents, including antibacterial agents. The present invention solves these problems by improving the total uptake of active drug into the plasma, allowing for development of new classes of previously unavailable oral antimicrobial agents, allowing for "step-down therapy" (i.e. transitioning a patient receiving parenteral therapy to oral therapy) within the same antimicrobial class where this option presently doesn't exist, and meeting unmet medical needs for antimicrobial agents with poor safety or tolerability profiles due to issues related to low uptake in the gastrointestinal tract. The present invention additionally may result in improved stability of traditionally unstable compounds by protection of the active ingredient throughout the gut, and may provide enhanced pharmacokinetic and pharmacodynamic profiles and/or improved post-antibiotic effects.

In one aspect, the present invention provides pharmaceutical compositions for oral delivery of antimicrobial agents comprising (a) a biopolymer, which is preferably swellable and/or mucoadhesive when hydrated; (b) an antimicrobial agent entrained within, or ionically bound, to the biopolymer; and (c) a cationic binding agent ionically bound to at least one member selected from the group consisting of the biopolymer and the antimicrobial agent.

In other embodiments, the present invention provides pharmaceutical compositions for oral delivery of antimicrobial agents comprising (a) a biopolymer, which is preferably swellable and/or mucoadhesive when hydrated; (b) an antimicrobial agent entrained within, or ionically bound, to the biopolymer; (c) a cationic binding agent ionically bound to at least one member selected from the group consisting of the biopolymer and the antimicrobial agent; and (d) an absorption enhancer.

In certain aspects of the invention, the antimicrobial agent is selected from the group consisting of cephalosporins, glycopeptides, penicillins, monobactams, glycycyclines, macrolides, oxazolidinones, lipopeptides, carbapenems, aminoglycosides, antifungals, β-lactamase inhibitors and combinations thereof.

Biopolymers are known to those skilled in the art, and may vary depending on the desired properties. In various embodiments, the biopolymers used in the claimed invention may include carrageenan, xylan, chitin, chitosan, chondroitin sulfate, sodium alginate, carboxymethylcellulose, pectin, polysaccharides, polypropylene gylcols, polyethylene glycols, polyacetates, liposomes, fatty acid complexes, cyclodextrins, cycloamyloses, clathrates, cycloalkyl amyloses, polyxylose, gellan gums and polylactic acids. Preferred biopolymers are carrageenan and pectin.

The invention in additional embodiments includes a cationic binding agent, such as for example, a positively charged metal ion or cationic molecules, including calcium, magnesium, lithium, iron, copper, zinc, aluminum, manganese, chromium, cobalt, nickel, ammonium salts, quaternary ammonium salts and basic amino acids. In preferred embodiments, the cationic binding agent is calcium or zinc. Preferred amino acids include basic amino acids selected from the group consisting of arginine, lysine, histidine, and combinations thereof. Preferred quaternary ammonium salts are selected from the group consisting of benzalkonium derivatives, cetyl pyridinium derivatives, dodecyl-trimethyl ammonium salt derivatives, tetradecyl-trimethyl ammonium salt derivatives, and cetyl-trimethyl ammonium derivatives. Any combination of the above may be used.

In other embodiments, the invention may include an absorption enhancer, such as some form of lipophilic absorption enhancer, including, for example, lipids, gelucire, capric and/or caprylic acids, oleic acids, palmitic acids, stearic acids, Capmuls, for example, CAPMUL MCM 90 (a mixture of mono- and di-glycerides of saturated $C_8$-$C_{10}$ fatty acids with monoglyceride; Abitec, Corp.) or CAPMUL 8210 (similar to MCM, but with about 70% monoglycerides, solid gylcerides, sodium lauryl sulfate, fatty acids including mono-, di, or triglycerides, TWEEN 80 (polyoxyethylene sorbitan fatty acid esters), non-ionic surfactants, bile salts, and combinations thereof, as well as any other surfactants known by those skilled in the art. Capmul and gelucire are preferred.

In other embodiments, the antimicrobial agent is a cephalosporin selected from the group consisting of ceftiofur, cefipime, cefixime, cefoperazone, cefotaxime, cefpodoxime, ceftazidime, ceftizoxime, ceftriaxone, cefpirome, cefclidin, cefmenoxime, cefozoprane, and combinations thereof.

In certain preferred embodiments the antimicrobial agent is a lipopeptide such as daptomycin. Additionally preferred are lipopeptide analogs such as described in U.S. Ser. Nos. 09/738,742, 09/737,908, and 09/739,535, hereby incorporated by reference in their entirety. Other preferred antimicrobial agents are lactamase inhibitors.

In other embodiments the antimicrobial agent is an aminoglycoside selected from the group consisting of amikacin, gentamicin, tobramycin, polymixin-B, streptomycin, kanamycin and combinations thereof.

In yet other embodiments the antimicrobial agent is a glycopeptide selected from the group consisting of vancomycin, dalbavancin, oritavancin and combinations thereof, or a carbapenem selected from the group consisting of meropenem, imipenem, MK0826, R-115,685, J-114,870 and CP5068.

In embodiments where the antimicrobial agent is a monobactam, the agent may be aztreonam or carumonam.

In other embodiments, the antimicrobial agent is a penicillin such as piperacillin or amoxicillin, or a glycopeptide such as vancomycin or daptomycin. In still other embodiments, the preferred cephalosporin is ceftriaxone.

In yet other embodiments the antimicrobial agent is an antifungal agent, for example, selected from the group consisting of amphotericin B, echinocandins, and cancidas.

In various embodiments, the cationic binding agent may be ionically bound to the biopolymer forming a cationic binding agent-biopolymer complex and the antimicrobial agent may be entrained within the cationic binding agent-biopolymer complex. In other embodiments, the cationic binding agent may be ionically bound to the antimicrobial agent forming a cationic binding agent-antimicrobial complex and the cationic binding agent-antimicrobial complex is entrained within the biopolymer. Additionally, in some cases, the cationic binding agent may be complexed to the antimicrobial and the cationic binding agent may be further ionically bound to the biopolymer forming an antimicrobial-cationic binding agent-biopolymer bridge. In preferred embodiments the pharmaceutical compositions of the invention comprise carrageenan, ceftriaxone, and arginine.

In other embodiments, the claimed invention encompasses oral formulations for delivery of a pharmaceutical composition having a bipolymer, an antimicrobial agent entrained within or ionically bound to the biopolymer and a cationic binding agent entrained within or ionically bound to the biopolymer or the antimicrobial. The oral formulations may be tablets, capsules, liquids, suspensions and the like, and may preferably be enterically coated capsules, tablets or particles.

DETAILED DESCRIPTION OF THE INVENTION

As used herein the following terms shall have the assigned meanings:

It must be noted that, as used in this specification and the appended claims, singular forms of "a," "an," and "the" include plural references unless the content clearly dictates otherwise.

"Absorption Enhancer" shall mean any substance which is effective to increase the absorption of an antimicrobial agent through the mucosa relative to absorption without such agent.

"Biocompatible" shall mean any substance that is not toxic to the animal to be treated.

"Biopolymer" shall mean a biologically compatible polymer which can be naturally occurring or synthetic. Examples include carrageenan, xylan, chitin, chitosan, carboxymethylcellulose, pectin, polysaccharides, polypropylene glycols, polyethylene glycols, polyacetates, polylactic acids, liposomes, gellan gums, fatty acid complexes, cyclodextrins, cycloamyloses, clathrates, cycloalkyl amyloses and polyxylose.

"Capmul" as used herein shall mean a mono, di- or triglyceride of a $C_8$-$C_{18}$ fatty acid or a mixture of such glycerides.

"Poorly absorbable antimicrobial" shall mean any antimicrobial agent that exhibits low bioavailability in oral or other non-parenteral dosage form, typically due to relatively high hydrophilicity and/or ionization properties of the antimicrobial agent. The antimicrobial agent can be positively charged, negatively charged, zwiterionic or amphiphilic.

"Oral absorption" is used to describe the manner in which the compositions of the present invention are delivered to the subject and the active ingredients absorbed into the blood. Typically, the composition is administered orally and the antimicrobial agent of the composition then crosses a mucosal membrane of the gastro-intestinal tract, preferably in the intestines. However, other methods of contacting the compositions of the present invention with the mucosal membrane of the gastro-intestinal tract may be used.

"Metal ion" or "metal cation" shall mean any positively charged metal ion that is functional for use with the present invention. Essentially, the metal cation binds to the antimicrobial agent and/or the biopolymer in accordance with the present invention. The metal cation may be complexed, chelated, or ionically bound to the antimicrobial agent. Exemplary metal cations include, but are not limited to calcium, potassium, magnesium, iron, copper, zinc, aluminum, manganese, chromium, cobalt, nickel, sodium, and combinations thereof.

"Cationic molecule" shall mean any molecule with one or more positively charged moieties that act to ionically bind to the antimicrobial agent and/or the biopolymer. Negatively charged moieties can also be present, though this is not required. Exemplary cationic molecules include cationic polymers, basic amino acids, quaternary ammonium salts, ammonium salts and combinations thereof.

"Cationic binding agent" is intended to include both metal cations and cationic molecules.

"Swellable" shall mean that the biopolymers and/or compositions of the present invention have the ability to swell or enlarge, such as when hydrated.

"Mucoadhesive" shall mean any biopolymer that is capable of adhering to a mucosal membrane, particularly when hydrated.

"OCTX" as used herein refers to a complex comprising ceftriaxone, a biopolymer and a cationic binding agent.

The claimed invention provides methods and compositions for treating infections in humans and other animals (collectively referred to as "animals" herein) by providing for the increased absorption of oral antimicrobial agents. In general, the compositions of the invention comprise a pharmaceutical composition for oral administration to a human or other animal comprising an antimicrobial agent, a biopolymer, and a cationic binding agent which is ionically bound to at least one of the biopolymer or the antimicrobial agent. The absorption of antimicrobial agents is significantly enhanced by the compositions and methods of the present invention. Although not limited to any particular mechanism of action, the claimed invention may enhance the stability of the antimicrobial agent, and partially neutralize the ionic charge (especially relevant for the readily ionizable third generation cephalosporins) thereby facilitating mucosal absorption through the intestinal wall. The intestinal absorption of these antibacterial agents may be enhanced for any oral formulation, including for example, solid, liquid, emulsion and suspension dosage forms.

In certain embodiments the claimed invention provides a pharmaceutical composition for oral delivery of an antimicrobial agent comprising (a) a biopolymer (b) an antimicrobial agent entrained within, or ionically bound to, the biopolymer; and (c) a cationic binding agent ionically bound to at least one of the biopolymer or the antimicrobial agent. Such compositions can be prepared for oral dosage in, for example, solid, liquid, emulsion or suspension forms. Additionally, the present invention provides methods for the delivery of therapeutic or prophylactic antimicrobial agents to the bloodstream of an animal comprising the steps of (a) orally administering to an animal a pharmaceutical composition comprising a biopolymer, an effective amount of a antimicrobial agent entrained within, or ionically bound, to the biopolymer, and a cationic binding agent ionically bound to at least one of the biopolymer or the antimicrobial agent; (b) causing the biopolymer to swell and adhere to a mucosal membrane lining of an intestinal wall of the animal such that the antimicrobial agent, and in certain embodiments, the cationic binding agent, in the composition will be delivered to the mucosal membrane lining, cross the intestinal wall and enter the bloodstream. In preferred methods of delivering the pharmaceutical composition to be administered additionally comprises an absorption enhancer.

In yet other embodiments the claimed invention encompasses methods of treating an animal by administering to an animal in need thereof a (1) pharmaceutical composition having an antimicrobial agent, a cationic binding agent and a biopolymer, and (2) an absorption enhancer.

Antimicrobial Agents:

One skilled in the art can readily determine the desired antimicrobial agent to be used in the claimed compositions and methods, as well as the dosage to be administered. This determination may be based upon a multitude of factors, including, but not limited to the infection to be treated, the pharmacokinetics and pharmacodynamics of the antimicrobial agent, the identity and susceptibility of the infecting microbe, the severity of the infection and the age and medical history of the animal to be treated.

In preferred embodiments, the antimicrobials of the invention are selected from the group consisting of cephalosporins, aminoglycosides, carbapenems, β-lactamase inhibitors, antifungals, penicillins, lipopeptides, glycopeptides, monobactams, and oxazolidinones.

Preferred antimicrobials of the invention include, but are not limited to cephalosporins, such as, for example, ceftiofur, cefipime, cefixime, cefoperazone, cefotaxime, cefpodoxime, ceftazidime, ceftizoxime, ceftriaxone, cefmenoxime, cefozoprane, cefpirome, and cefclidin. Additionally, MRSA-active cephalosporins which are in development stages such as RO 65-5788 (U.S. Pat. No. 6,232,306, hereby incorporated by reference in its entirety), RWJ-54428 (U.S. Pat. No. 6,025,352, hereby incorporated by reference in its entirety), RWJ-333441 (Curr. Opin. Invest. Drugs (2001); 2 (2) 209-211, hereby incorporated by reference) are appropriate for use in the invention. Additionally, cephalosporins such as described in U.S. Pat. No. 6,093,813 (hereby incorporated by reference) are useful. The most preferred cephalosporin is ceftriaxone, such as described in U.S. Ser. No. 09/598,089 (to be issued as U.S. Pat. No. 6,248,360), and U.S. Ser. No. 09/829,405.

In other embodiments, the antimicrobials of the invention can be selected from aminoglycosides, such as, for example amikacin, gentamicin, tobramycin, polymixin-B, streptomycin, and kanamycin. The agent may in some embodiments be a glycylcline.

In other preferred embodiments, the antimicrobials to be used in the claimed invention are carbapenems, such as for example, one or more selected from the group consisting of meropenem, imipenem, MK0826 (Invanz, WO 99/45010, hereby incorporated by reference), R-115,685 (Sankyo, WO 01/02401 hereby incorporated by reference), J-114,870 (Banyu, WO 99/31106 hereby incorporated by reference) and CP-5068 (Meiji, see R&D Focus, Feb. 19, 2001; IMS World Publications).

Additionally, the compounds of the invention may be a lactamase inhibitor such as tazobactam, oxapenem, clavulanic acid, sublactam, or, for example, Zosyn®, which is a combination of tazobactam and pipericillin marketed by Wyeth-Ayerst.

Lipopeptides such as daptomycin, and the analogs disclosed in U.S. Ser. Nos. 09/738,742, 09/737,908, and 09/739,535, hereby incorporated by reference in their entirety.

Additional antimicrobials which are preferred include glycopeptides such as vancomycin, dalbavancin and oritavancin, monobactams such as aztreonam or carumonam.

In some embodiments the antimicrobial agent of the invention comprises an anti-fungal agent, such as for example, amphotericin B, echinocandins and cancidas.

In other embodiments, penicillins are preferred, such as, for example, piperacillin and amoxicillin.

Most preferred are ceftriaxone (Formula 1) and daptomycin (Formula 2). Ceftriaxone is a poorly absorbable antibiotic, and thus, prior to the claimed invention, was not amenable to oral administration. The ceftriaxone molecule has several inherent characteristics which may contribute to its poor oral bioavailability, including for example, its polarity and hydrophobicity, and the fact that it is unstable in the presence of acid and peptidases by virtue of the presence of peptide bonds. The ceftriaxone salt of formula 1 is most preferred.

Formula 1

Daptomycin (shown in formula 2) is a lipopeptide described in detail in U.S. Pat. No. 5,912,226 (and referred to therein as LY 146032), herein incorporated by reference in its entirety. Additionally preferred are lipopeptide analogs such as described in Pending U.S. Ser. Nos. 09/738,742, 09/737,908, and 09/739,535, hereby incorporated by reference in their entirety.

Formula 2

Biopolymers:

The claimed invention may comprise any biopolymer that is not toxic to the animal to be treated, and provides for the desired characteristics of the pharmaceutical composition. However, mucoadhesive and/or swellable biopolymers are the most preferred. Exemplary biopolymers include, but are not limited to, carrageenans, pectins, chondroitin sulfate, sodium alginate, and/or polymethacrylic acid, xylan, hyaluronic acid, chitin, chitosan, chondroitin sulfate, sodium alginate, carboxymethylcellulose, pectin, polysaccharides, polypropylene glycols, polyethylene glycols, polyacetates, liposomes, fatty acid complexes, cyclodextrins, cycloamyloses, clathrates, cycloalkyl amyloses, polyxylose and polylactic acids. Carrageenan and pectin are most preferred.

Carrageenan is the general term used to describe hydrophilic polysaccharides extracted from a number of closely related species of red seaweeds that are highly sulfated, linear molecules having a galactose backbone. There are three different types of carrageenan, Kappa, Lambda and Iota, which are differentiated by the amount of 3,6-anhydrogalactose residues and number and position of the sulfate groups. For example, the following carrageenans can be obtained from FMC Biopolymer: Gelcarin® GP 379 (Iota) and Gelcarin® GP 911 (Kappa). The carrageenan may have a calcium content of about 3.6% by weight.

The preferred carrageenan for certain compositions of the invention is a carrageenan having a low calcium content, i.e a calcium content of from about 0 to about 3%, more preferably about 0-2%, and most preferably about 0.1-1% calcium by weight. The most preferred carrageen has a sodium content of about 0.4% or less, such as, for example, Viscarin® XP (FMC Biopolymer). In certain compositions, processing with other carrageenans resulted in undesired precipitation of the active antimicrobial agent. Most preferred compositions comprise ceftriaxone as the antimicrobial agent, low calcium carrageenan, calcium, and Capmul. OCTX2 as defined in Example 2 is most preferred.

Cationic Binding Agents:

Any cationic binding agent can be used in the claimed invention, and preferred cationic binding agents include for example, any positively charged metal ion, or any charged cationic molecules, such as, for example, calcium, potassium, magnesium, lithium, iron, copper, zinc, sodium, aluminum, manganese, chromium, cobalt, nickel, ammonium salts, quaternary ammonium salts such as benzalkonium derivatives, cetyl pyridinium derivatives, dodecyl-trimethyl ammonium salt derivatives, tetradecyl-trimethyl ammonium salt derivatives and cetyl-trimethyl ammonium salt derivatives. Additionally, basic amino acids such as arginine, lysine and histidine are preferred cationic binding agents.

Preferred metal cations include, for example, calcium, potassium, magnesium, iron, copper, zinc, aluminum, manganese, chromium, cobalt, nickel, and/or sodium. These cations are preferred because each of these metal cations are biocompatible. However, cations such as zinc, and particularly, calcium are most preferred.

The metal cation can be arranged in relation to the biopolymer and the poorly absorbable antimicrobial agent in one of three preferred manners. First, the metal cation can be bound to the biopolymer forming a cation-biopolymer combination such that the antimicrobial agent is entrained within the cationic-biopolymer ionic combination. Second, the metal cation can be complexed to the antimicrobial agent and the cation-antimicrobial agent complex can then be entrained within the biopolymer. Third, the metal cation can be complexed to the antimicrobial agent and further bound to the biopolymer forming an antimicrobial agent-cation-biopolymer bridge. When using the metal cation as the binding agent, the compositions of the present invention may be prepared in both solid form (e.g., tablets, capsules, etc.), liquids, emulsions and suspension form. The formulations in other embodiments may comprise granules which are compacted into tablet form, or placed in capsules.

If a cationic molecule is used as the binding agent (rather than the metal cation), then there are three preferred molecular types that may be used. First, cationic polymers including, but not limited to, poly(allylamine), poly-(l-lysine), poly(arginine) and dodecyltrimethylammonium bromide. Also polyethylenimines (primary, secondary, and tertiary) may be used.

Further, the cationic molecule may be a quaternary ammonium salt including, but not limited to, benzalkonium derivatives, cetylpyridinium derivatives such as chlorides or bromides, dodecyl-trimethyl ammonium salt derivatives, tetradecyl-trimethyl ammonium salt derivatives, and/or cetyl-trimethyl ammonium salt derivatives.

Lipids

Preferred compositions comprise an absorption enhancer, such as a lipid or, alternatively, comprise a polymer or antimicrobial agent having lipid-like properties. For example, the compositions described in Example 7 contain cetylpyridinium, which, in addition to providing a positive charge, may contribute lipid-like properties to the composition, and therefore the desired effect can be seen in the absence of adding a lipid to the composition.

Frequently used absorption enhancers include for example, lipids, gelucire, capric and caprylic acids, oleic acids, palmitic acids, stearic acids, Capmuls, for example, CAPMUL MCM 90 (a mixture of mono- and di-glycerides of saturated $C_8$-$C_{10}$ fatty acids with monoglyceride; Abitec, Corp.) or CAPMUL 8210 (similar to MCM, but with about 70% monoglycerides). Capmul is preferred, and can be present in the composition in any desired ratio, preferably from 12:1 to 1:1 capmul:OCTX by weight. Alternatively, any known absorption enhancers may be used, including any mixtures of the above. Capmul and gelucire are preferred.

With each of these compositions and methods, the antimicrobial agent and binding agent can be present within a specific preferred molar ratio, though these ratios are not intended to cover all effective compositions. For example, if a metal cation is used as the binding agent, then the antimicrobial agent to metal cation molar ratio can be from about 30:1 to 1:5, preferably about 20:1 to 5:1, and most preferably, about 20:1 by weight. Additionally, the antimicrobial agent to biopolymer molar ratio can be from about 5:1 to 1:5, preferably about 2:1. Alternatively, if a cationic molecule is used as the binding agent, then the antimicrobial agent to cationic molecule molar ratio can be from about 1:4 to 1:1, preferably from about 1:2 to 1:1, e.g., 1:2 for antimicrobial agent:amino acid embodiments and 1:1 for antimicrobial agent:cetyl pyridinium embodiments. Additionally, in this embodiment, the antimicrobial agent to biopolymer molar ratio can be from about 5:1 to 1:5, preferably about 2:1.

Formulations

The compositions of the invention are formulated for oral administration to an animal, and preferably may be in solid formulations such as tablets and capsules. Sustained release or enterically coated preparations may also be devised. For pediatric and geriatric applications, emulsions, suspensions, syrups and chewable tablets may be especially suitable. For oral administration, the claimed pharmaceutical compositions are in the form of, for example, a tablet, capsule, suspension or liquid. The composition is preferably in the form of a dosage unit containing a therapeutically-effective amount of the antimicrobial agent. The tablets and capsules of the invention can contain, in addition to the active ingredients, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants for example, magnesium stearate, polyethylene glycol, silica or talc; disintegrants, for example, potato starch, flavoring or coloring agents, or acceptable wetting agents. Oral liquid preparations generally may be in the form of aqueous or oily solutions, suspensions, emulsions, syrups or elixirs, and may contain conventional additives such as suspending agents, emulsifying agents, non-aqueous agents, preservatives, coloring agents and flavoring agents. In either case, the composition is designed such that the antimicrobial agent may be transmucosally delivered into the bloodstream, preferably through the walls of the small intestines.

In certain embodiments the claimed compositions may comprise more than one antimicrobial agent. This is especially useful when treating infections resulting from more than one infecting microbial organism.

Factors to be considered in choosing the appropriate antimicrobial agent to be used in the invention include, for example, the identity of the infecting organism, the antimicrobial susceptibility (or potential susceptibility) of the infecting organism, and a variety of factors related to the animal to be treated, including, for example, patient history, age, site and severity of infection, etc. Additional considerations include the pharmacokinetic and pharmacodynamic properties of the antimicrobial agent. Oral compositions may take such forms as tablets, capsules, oral suspensions and oral solutions. The oral compositions may utilize carriers such as conventional formulating agents, and may include sustained release properties as well as rapid delivery forms.

Capsules are preferred. Any capsule material known in the art can be used depending upon the desired dissolution characteristics of the pharmaceutical compositions. For example, capsules may comprise hydroxypropylmethylcellulose, a mixture of polyethylene glycol with hydroxypropylmethylcellulose, gelatin or agar.

Preferably, the compositions of the invention are formulated with enteric coatings in order to prevent the degradation of the antimicrobial agent by the acidity of the gastric fluid and optimize delivery of the active agent to the desired location in the intestine. Capsules can be coated with selected materials depending upon the desired capsule characteristics, and may include, for example, cellulose acetate phthalate, hydroxypropyl methylcellulose phthalate, polyvinyl acetate phthalate, shellac, methacrylic acid and esters thereof, zein, or other materials known in the art. The enteric coating materials may be applied with or without plasticizers, such as acetylated glycerides, triethyl citrate, propylene glycol or diethylphthalates. Preferred coating materials are those which dissolve at a pH of 5 or above. The coatings therefore only begin to dissolve when they have left the stomach and entered the small intestine. A thick layer of coating is provided which will dissolve in about fifteen minutes thereby allowing the capsule underneath to breakup only when it has reached the duodenum. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy in his article "Enteric Coatings and Delayed Release" Chapter 7 in Drug Delivery to the Gastrointestinal Tract, editors Hardy et al., Ellis Horwood, Chichester, 1989. For coatings of cellulose esters, a thickness of 200-250 μm would be suitable.

Especially preferred materials are methylmethacrylates or copolymers of methacrylic acid and methylmethacrylate. Such materials are available as EUDRAGIT™ polymers (Rohhm Pharma, Darmstadt, Germany). Eudragits are copolymers of methacrylic acid and methylmethacrylate. Preferred compositions are based on EUDRAGIT L 30 D-55, EUDRAGIT L1W-55, EUDRAGIT™ L100 and Eudragit S100. EUDRAGIT L30-D55 AND L1W-55 dissolve at pH≧5.5. EUDRAGIT™ L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Preferred coating compositions are based on EUDRAGIT™ L100 and EUDRAGIT™ S100 in the range 100 parts L100:0 parts S100 to 20 parts L100:80 parts S100. The most preferable range is 70 parts L100:30 parts S100 to 80 parts L100:20 parts S100. As the pH at which the coating begins to dissolve increases, the thickness necessary to achieve colon specific delivery decreases. For formulations where the ratio of EUDRAGIT™ L100:S100 is high, a coat thickness of the order 150-200 μm is preferable. This is equivalent to 70-110 mg of coating for a size 0 capsule. For coatings where the ratio EUDRAGIT™ L100:S100 is low, a coat thickness of the order 80-120 μm is preferable, equivalent to 30 to 60 mg coating for a size 0 capsule.

Most preferred is EUDRAGIT L30-D55, for delivery in the duodenum (i.e. ≧5.5 pH and less than 6.8.)

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound. Preferred dosages for example, for the administration of ceftriaxone compositions may be from about 0.25 to about 8 grams per day, more preferably about 2 to about 4 grams per day. The dosage intervals can be determined by one skilled in the art, and may for example, be every 6 to every 24 hours. Preferred dosages for the administration of daptomycin compositions according to the invention, for example, are in the range of from about 2 to about 15 mg/kg, more preferably about 8-10 mg/kg day.

The compositions of the invention are useful in methods of treating subjects having an infection. The term "treating" is used to denote both the prevention of an infection and the control of an established infection once the host animal has become infected. The methods of the invention comprise administering to a human or other animal a therapeutically or prophylactically effective amount of the antimicrobial agent. "Therapeutically effective amount" means an amount of antimicrobial agent sufficient to prevent the onset, alleviate the symptoms, or stop the progression of a microbial infection. The compositions of the invention can be administered as a single daily dose or in multiple doses per day. The treatment regime may require administration over extended periods of time, e.g. for several days or for several weeks. The amount per administered dose or the total amount administered will depend on such factors as the nature and severity of the infection, the age and general health of the patient, the tolerance of the patient to the antimicrobial agent and the microorganism or microorganisms involved in the infection. For example, in certain embodiments, the compositions of the invention can be used to treat respiratory tract infections, skin and soft tissue infections, urinary tract infections, sinusitis, sexually transmitted diseases, endocarditis, bacteremia, osteomyelitis, septicemia and lyme disease.

In certain embodiments, the claimed invention encompasses a method of treating an animal comprising the steps of (1) administering to the animal a pharmaceutical composition comprising a biopolymer, an antimicrobial agent, and a cationic binding agent, and (2) an absorption enhancer. In other embodiments, the claimed invention encompasses methods of treating an animal comprising administering to the animal a pharmaceutical composition comprising a biopolymer, an antimicrobial agent, a cationic binding agent and an absorption enhancer.

The following examples are not intended to be limiting and further exemplify various embodiments of the claimed invention.

EXAMPLES

1. Preparation of OCTX1

About 400 mg of carrageenan was added to 80 ml of an aqueous solution at approximately 55° C. The solution was then mixed by magnetic stirrer at room temperature until the carrageenan was essentially fully swollen. Next, an aqueous solution containing $Ca^{2+}$ ions was prepared by dissolving 44.5 mg (0.33 mole) of calcium chloride in 10 ml of water. An aqueous solution of CTX was prepared by dissolving 1.0 g of ceftriaxone sodium in 10 ml of water. The entire volume of CTX and $CaCl_2$ solutions were simultaneously added dropwise to the CG solution. The dispersion was centrifuged and the supernatant removed for subsequent lyophilization to dryness. The resulting composition comprises Carrageenan 0.4 g (27.7%), Ceftriaxone 1 g (69.2%), Calcium Chloride 0.0445 g (3.1%), and can be milled to yield a fine powder.

2. Preparation of OCTX2

An aqueous solution of calcium chloride is prepared by dissolving approximately 0.0114 g of $CaCl_2$ in 80 ml of an aqueous solution. About 400 mg of low calcium carrageenan (<0.4% $Ca^{++}$) is hydrated in the $CaCl_2$ solution. Then 1.0 g of ceftriaxone is dissolved in 20 ml of water and added to the solution at room temperature. The resulting composition comprises 69.2% ceftriaxone, 28.4% low calcium carrageenan and 0.7% $CaCl_2$.

3. Preparation of a CTX-ZN-CG Complex

About 400 mg of carrageenan was added to 80 ml of an aqueous solution containing 1.0 g (1.67 mole) of ceftriaxone. The solution was then mixed by magnetic stirrer at room temperature until the carrageenan was essentially fully swollen, forming a ceftriaxone-carrageenan hydrogel. Next, an aqueous solution containing zinc ions was prepared by dissolving 45 mg (0.33 mole) of zinc chloride in 20 ml of water. The entire aqueous solution was then dropped into the ceftriaxone-carrageenan hydrogel or suspension. The complex was then stirred by a magnetic stirrer at room temperature for 2 hours. This resulted in the formation of a ceftriaxone-zinc-carrageenan gel complex. The ceftriaxone-zinc-carrageenan gel was then freeze-dried while in the swollen state. About 1.4 grams of a ceftriaxone-zinc-carrageenan complex was obtained.

About 40 mg CTX eq./kg of the ceftriaxone-zinc-carrageenan complex was suspended in water and i.d. administered with 0.2 ml of capmul per rat (wgt about 300 g) to four rats. At specific time intervals, 0.6 ml of blood was taken from each rat and centrifuged. About 0.2 ml of the blood plasma was then analyzed for CTX by HPLC. The results are represented in Table 1 below:

TABLE 1

| Time After i.d. Dosage (minutes) | Average Plasma Concentration of CTX (μg/ml) |
|---|---|
| 30 | 17 |
| 60 | 16 |

TABLE 1-continued

| Time After i.d. Dosage (minutes) | Average Plasma Concentration of CTX (µg/ml) |
|---|---|
| 90 | 17 |
| 120 | 13 |
| 180 | 14 |
| 240 | 8 |

4. Preparation of a CTX-ARG-CG Complex

About 582 mg (3.34 mole) of arginine was dissolved in 50 ml of distilled water. Additionally, about 1.0 grams (1.67 mole) of ceftriaxone was dissolved in 50 ml of a separate volume of distilled water. The solution containing arginine was adjusted with 1N—HCl until the pH reached 6.0. The ceftriaxone solution was then added to the arginine solution and mixed by a magnetic stirrer at room temperature for 1 hour forming a ceftriaxone-arginine solution. To the ceftriaxone-arginine solution was added about 400 mg of carrageenan and the solution was mixed by magnetic stirrer at room temperature for 2 hours. A ceftriaxone-arginine-carrageenan complex was formed which was freeze-dried while in the swollen state, yielding about 1.84 g of the freeze dried complex.

About 40 mg CTX eq./kg of the ceftriaxone-arginine-carrageenan complex described above was suspended in water and i.d. administered with 0.2 ml of capmul to four rats. At specific time intervals, 0.6 ml of blood was taken from each rat and centrifuged. About 0.2 ml of the blood plasma was then analyzed for CTX by HPLC. The results are represented in Table 2 below:

TABLE 2

| Time After i.d. Dosage (minutes) | Average Plasma Concentration of CTX (µg/ml) |
|---|---|
| 30 | 57 |
| 60 | 39 |
| 90 | 26 |
| 120 | 20 |
| 180 | 13 |
| 240 | 9 |

About 610 mg (3.34 mole) of lysine was dissolved in 50 ml of distilled water. Additionally, 1.0 gram (1.67 mole) of ceftriaxone was dissolved in 50 ml of a separate volume of distilled water. The solution containing arginine was adjusted with 1N—HCl until the solution reached pH 6.0. The ceftriaxone solution was then added to the lysine solution and stirred by a magnetic stirrer at room temperature for 1 hour forming a ceftriaxone-lysine solution. To the ceftriaxone-lysine solution was added about 400 mg of carrageenan and the solution was stirred by magnetic stirrer at room temperature for 2 hours. A ceftriaxone-lysine-carrageenan hydrogel was formed. The hydrogel was then freeze-dried while in the swollen state, yielding about 1.92 g of the freeze-dried complex.

About 40 mg CTX eq./kg of the ceftriaxone-lysine-carrageenan complex described was suspended in water and i.d. administered with 0.2 ml of capmul to four rats. At specific time intervals, 0.6 ml of blood was taken from each rat and centrifuged. About 0.2 ml of the blood plasma was then analyzed for CTX by HPLC. The results are represented in Table 3 below:

TABLE 3

| Time After i.d. Dosage (minutes) | Average Plasma Concentration of CTX (µg/ml) |
|---|---|
| 30 | 14 |
| 60 | 6 |
| 90 | 5 |
| 120 | 4 |
| 180 | 3 |
| 240 | 2 |

6. Preparation of CTX-HIS-CG Complex

About 518.4 mg (3.34 mole) of histidine was dissolved in 50 ml of distilled water. Additionally, about 1.0 grams (1.67 mole) of ceftriaxone was dissolved in 50 ml of a separate volume of distilled water. The solution containing histidine was adjusted with 1N—HCl until the solution reached pH 5.5. Next, the ceftriaxone solution was added to the histidine solution and stirred by a magnetic stirrer at room temperature for 1 hour forming a ceftriaxone-histidine complex solution. About 400 mg of carrageenan was added to ceftriaxone-histidine solution and stirred by magnetic stirrer at room temperature for 2 hours. After the stirring was complete, a white suspension was formed in the hydrogel. The ceftriaxone-histidine-carrageenan hydrogel in a swollen state was rapidly freeze-dried using a dry-ice-acetone mixture. About 1.75 g of product was produced.

7. Preparation of a CTX-CP-CG Complex

About 210 mg (0.62 mole) of particulate cetylpyridinium chloride was dissolved in 50 ml of distilled water. Additionally, about 378 mg (0.62 mole) of ceftriaxone was dissolved in 50 ml of a separate volume of distilled water. Next, the ceftriaxone solution was added to the cetylpyridinium chloride solution and stirred by a magnetic stirrer at room temperature for 1 hour forming a ceftriaxone-cetylpyridinium chloride solution. About 400 mg of carrageenan was added to the ceftriaxone-cetylpyridinium chloride solution and the solution was stirred by magnetic stirrer at room temperature for 2 hours. A ceftriaxone-cetylpyridinium chloride-carrageenan hydrogel complex was formed. The complex was then freeze-dried, yielding about 0.86 g of the freeze-dried complex.

About 40 mg CTX eq./kg of the ceftriaxone-cetylpyridinium chloride-carrageenan complex described above was suspended in water and i.d. administered without capmul to four rats. At specific time intervals, 0.6 ml of blood was taken from each rat and centrifuged. About 0.2 ml of the blood plasma was then analyzed for CTX by HPLC. The results are represented in Table 4 below:

TABLE 4

| Time After i.d. Dosage (minutes) | Average Plasma Concentration of CTX (µg/ml) |
|---|---|
| 30 | 28 |
| 60 | 30 |
| 90 | 29 |
| 120 | 27 |
| 180 | 25 |
| 240 | 21 |

8. Preparation of CTX-Ca-CG 400 mgs of carrageenan (CG) was added into 80 ml distilled water at 50° C. and stirred until fully hydrated. 10 ml of ceftriaxone solution and 10 ml of various concentrations of $CaCl_2$ solution were added dropwise into the CG solution simultaneously and stirred for additional 30 minutes at 50° C. The formed CTX-Ca-CG was centrifuged at 5,000 rpm for 10 min and the supernatant was freeze-dried. The amount of CTX in the formulation was analyzed by UV-VIS spectroscopy ($\lambda$max-272 nm).

9. Preparation of CTX-Ca-PT 400 mgs of pectin (PT) was added into 80 ml. distilled water at 50° C. and stirred until fully swollen. 10 ml of ceftriaxone solution and 10 ml of various concentrations of $CaCl_2$ solution were added dropwise into the PT solution simultaneously and stirred for an additional 30 minutes at 50° C. The formed CTX-Ca-PT was freeze-dried. The amount of CTX in the formulation was analyzed by UV-VIS spectroscopy ($\lambda$max-272 nm).

Intravenous Administration to Rats

Male Srague Dawley rats weighing 250-300 g with free access to water were fasted for about 18 hr. prior to the experiment. These rats were anesthetized with 5.0 mg/100 g of pentobarbital by intraperitoneal injection. Ceftriaxone was dissolved in distilled water to achieve a final concentration of 20 mg/kg and injected into a jugular vein. Blood samples were collected through the jugular vein catheter at predetermined time intervals.

Intraduodenal Administration to Rats

To determine absorption from the intestine, male Sprague Dawley rats weighing 250-300 g with free access to water were fasted for about 18 hours prior to the experiment. These rats were anesthetized and maintained with Ketamine/Xlazine ((60 mg/kg)/(80 mg/kg)) by intraperitoneal injection. The small intestine was exposed by a midline abdominal incision. A small incision was made in the stomach to insert a polyethylene tube (i.d. 0.76 mm, o.d. 1.22 mm, Clay Adams) toward the duodenum, which was closed at the exposed end by a stopcock to prevent drainage of drug solution from the duodenum. Ceftriaxone and oral formulations of CTX were dissolved in distilled water to achieve a final concentration of 40 mg CTX eq./kg and injected into the duodenum using the tube. Then 0.2 ml mono- and diglyceride mixture (Capmul) was coadministered into the duodenum using the intraduodenal tube. Blood samples were taken with a heparinized syringe through the jugular vein catheter at predetermined intervals.

Analysis of Ceftriaxone

The concentration of ceftriaxone in the plasma was determined by HPLC. Blood samples were centrifuged for 5 min at 5,000 rpm and 0.2 ml of plasma was taken into the microtube. 0.2 ml plasma was diluted by 0.2 ml of distilled water, and then 0.8 ml of acetonitrile was added for protein removal. The resulting suspensions were centrifuged for 10 min at 12,000 rpm and 50 µl of the clear supernatant was used for HPLC analysis. The i.v. and i.d. data were analyzed by Pharsight Winnonlin ver 3.0 to obtain Cmax, Tmax, $AUC_{0-4\ hours}$, and $AUC_{inf}$ from plasma concentration-time curve. Percent bioavailability was calculated as follows: % BA=(AUC i.d./AUC i.v.)×(Dose i.v./Dose i.d.)×100

TABLE 5

Pharmacokinetic Data of Ceftriaxone (CTX) after i.d. administration of various CTX-CA-CG in rats. All but i.v. received 0.2 ml. capmul chase.

| sample | Cmax (µg/ml) | Tmax (hr) | $AUG_{0-4\ hr}$ (µghr/ml) | $AUC_{00}$ (µghr/ml) | $BA_{0-4\ hr}$ (%) | $BA_{00}$ (%) |
|---|---|---|---|---|---|---|
| i.v. CTX | — | — | 1.68.2 ± 29.4 | 188.0 ± 6.4 | — | — |
| i.d. CTX | 17.2 | 1.0 | 31.7 ± 12.4 | 52.3 ± 32.4 | 9.4 | 13.9 |
| CTX1-CG4 | 15.32 | 0.67 | 33.7 ± 19.5 | 47.4 ± 25.8 | 10.0 | 12.68 |
| CTX1-Ca0.1-CG4 | 36.96 | 1.0 | 82.8 ± 36.5 | 106.0 ± 44.4 | 24.6 | 28.2 |
| Ca 0.2-CG4 | 69.1 | 0.5 | 124.3 ± 0.5 | 136.0 ± 0.1 | 24.6 | 28.2 |
| CTX1-Ca0.5-CG4 | 14.0 | 0.5 | 20.6 ± 4.5 | 22.7 ± 5.1 | 6.1 | 6.8 |
| Ca1-CG4 | n.a | n.a | n.a | n.a | n.a | n.a. | i.d. CTX: control; n.a.: no absorption
i.v. dose: 20 mg CTX/kg, i.d. dose: 40 mg CTX eq/kg.
ratios are relative amounts as follows: CTX g-Ca M-CG mg

TABLE 6

Pharmacokinetic data of Ceftriaxone after i.d. administration of various CTX-Ca-Pectin in rats. All but i.v. received 0.2 ml capmul chase

| sample | Cmax (µg/ml) | Tmax (hr) | $AUC_{0-4\ hr}$ (µghr/ml) | $AUC_{00}$ (µghr/ml) | $BA_{0-4\ hr}$ (%) | $BA_{00}$ (%) |
|---|---|---|---|---|---|---|
| i.v. CTX | — | — | 1.68.2 ± 29.4 | 188.0 ± 6.4 | — | — |
| i.d. CTX | 17.2 | 1.0 | 31.7 ± 12.4 | 52.3 ± 32.4 | 9.4 | 13.9 |
| CTX1-PT4 | 57.3 | 0.5 | 105.5 ± 32.6 | 128.8 ± 29.6 | 29.9 | 38.3 |
| CTX1-Ca0.2-PT4 | 67.43 | 0.678 | 133.6 ± 48.1 | 224.0 ± 131.7 | 40.6 | 66.6 |
| PT8 | 27.51 | 0.5 | 46.5 ± 22.2 | 54.6 ± 29.3 | 13.8 | 16.2 |
| CTX1-Ca0.4-PT4 | 54.8 | 0.5 | 81.6 ± 22.1 | 94.2 ± 24.0 | 24.2 | 28.0 | i.d. CTX: control; n.a.: no absorption
i.v. dose: 20 mg CTX/kg, i.d. dose: 40 mg CTX eq/kg.
ratios indicate relative amounts as follows: CTX g- Ca M - PT mg

Example 10

Plasma Concentration of Ceftriaxone Over Time in Rats after Intraduodenal (i.d.) Administration of a Ceftriaxone-Calcium-Carrageenan Complex About 40 mg ceftriaxone (CTX) eq./kg of the complex described in Example 1 was suspended in water and i.d. administered with 0.2 ml of capmul (an absorption enhancer) to four rats. At specific time intervals, 0.6 ml of blood was taken from each rat and centrifuged. About 0.2 ml of the blood plasma was then analyzed for CTX by HPLC. The results are represented in Table 7 below:

TABLE 7

| Time After i.d. Dosage (minutes) | Average Plasma Concentration of CTX (µg/ml) |
|---|---|
| 30 | 53 |
| 60 | 40 |
| 90 | 33 |
| 120 | 25 |
| 180 | 14 |
| 240 | 9 |

Example 11

Plasma Concentration of Ceftriaxone Over Time in Rats after Intraduodenal (i.d.) Administration of the CTX with Capmul as Control As a control, about 40 mg/kg of CTX was i.d. co-administered with 0.2 ml of capmul to four rats. See, *Chemotherapy* 34: 77-84 (1988). At specific time intervals, 0.6 ml of blood was taken from each rat and centrifuged. About 0.2 ml of the blood plasma was then analyzed for CTX by HPLC. The results are represented in Table 8 below:

TABLE 8

| Time After i.d. Dosage (minutes) | Average Plasma Concentration of CTX (µg/ml) |
|---|---|
| 30 | 10 |
| 60 | 11 |
| 90 | 9 |
| 120 | 7 |
| 180 | 6 |
| 240 | 5 |

Example 12

Plasma Concentration of Ceftriaxone Over Time in Rats after i.v. Administration

For comparison purposes, about 20 mg/kg of CTX was administered (i.v.) to four rats. At specific time intervals, 0.6 ml of blood was taken from each rat and centrifuged. About 0.2 ml of the blood plasma was then analyzed for CTX by HPLC. The results are shown in Table 9 below:

TABLE 9

| Study # | Test Article | Capmul: OCTX | Capmul: CTX | Capmul Conc. of Emulsion | Total Capmul Administered (g) | C max (µg/mL) | % Bioavailability |
|---|---|---|---|---|---|---|---|
| 103-2 | OCTX1 (C) | | 10:1 | N/A | | 36-57 | 48.5 |
| 103-6 | 1 = OCTX1 (E) | 1 = 1:1 | 1 = 2.2:1 | 1 = 21.6 mg/mL | | 1 = 5-7 | 3.3 |
| | 2 = OCTX2 (C) | 2 = 10:1 | 2 = 11:1 | 2 = N/A | | 2 = 44-55 | 44.6 |
| 103-7 | 1 = OCTX2 (E) | 1 = 5:1 | 1 = 9:1 | 1 = 97.8 mg/mL | | 1 = 43-49 | 47.9 |
| | 2 = OCTX2 (E) | 2 = 10:1 | 2 = 18:1 | 2 = 179.4 | | 2 = 19-39 | 23.6 |
| 103-8 | CTX-Capmul (E) | 5:1 | 6.25:1 | 62.5 mg/mL | | 14-30 | 14.6 |
| 103-9 | CTX-CG | 0 | 0 | 0 | | 0 | 0 |
| 103-10 | CTX-Capmul (E) | | 9:1 | | | 2.5-31 | |

(C)—Capmul chase
(E)—Capmul emulsion

Example 13

Preparation of Meropenem-Calcium-Carageenan Complex

Carrageenan was hydrated in water at a temperature of 50° C. or higher. Next, an aqueous solution containing $Ca^{2+}$ ions was prepared by dissolving calcium chloride in water. Similarly, a meropenem solution was prepared by addition of meropenem to water. The meropenem solution and the calcium solution were then added simultaneously to the carrageenan solution. The meropenem-calcium-carrageenan solution was lyophilized.

Plasma Concentration of Meropenem Over Time in Rats after Intraduodenal Administration of Meropenem-Calcium-Carrageenan Complex.

Meropenem was infused as a solution through an intraduodenal catheter followed by 0.2 ml. Capmul chase and a saline flush. The carrier formulation was meropenem in calcium-carrageenen to a final concentration of approximately 55% meropenum by weight. Two rats were dosed through a duodenum catheter and plasma samples were collected through 4 hours post dosage. For comparison purposes, a control group received meropenem reconstituted according to the manufacturers instructions, and infused as a solution through ID catheter followed by a saline flush.

Two fasted rats were dosed through a duodenal catheter and plasma samples were collected through 4 hours post dosage. These results show that meropenem was not absorbed and blood concentrations remained undetectable when prepared according to the art. A third rat expired prior to dosage, possibly due to anesthesia required for surgery. Rat #1 expired at 4 hours, possibly due to the effects of prolonged anesthesia and blood collection.

| Animal | $C_{max}$ (@g/ml) | $AUC_{0-4\ hr}$ (@g × hr/ml) | $T_{1/2}$ (minutes) |
|---|---|---|---|
| Rat 1 | 5.98 | 5.54 | 35.2 |
| Rat 2 | 2.83 | 1.44 | 19.7 |

Meropenem was rapidly absorbed and reached peak concentrations at the first time point (15 minutes) samples. IV dosage (in progress) will allow calculation of fraction absorbed (F %). AUC values of 1.4 and 5.4 @gxhr/ml suggest an oral F % of <5%, assuming an IV dosage of 10 mg/kg would generate an AUC of >30 @gxhr/ml.

The data show that meropenem was rapidly absorbed and reached peak concentrations at the first time point (15 minutes) samples. IV dosage will allow calculation of fraction absorbed. AUC values of 1.4 and 5.4 µgxhr/ml suggest an oral F % of <5%, assuming an IV dosage of 10 mg/kg would generate an AUC of >30 µgxhr/ml. Future trials will investigate absorption of naked meropenem and additional formulations.

Example 14

Daptomycin

Figure 1:
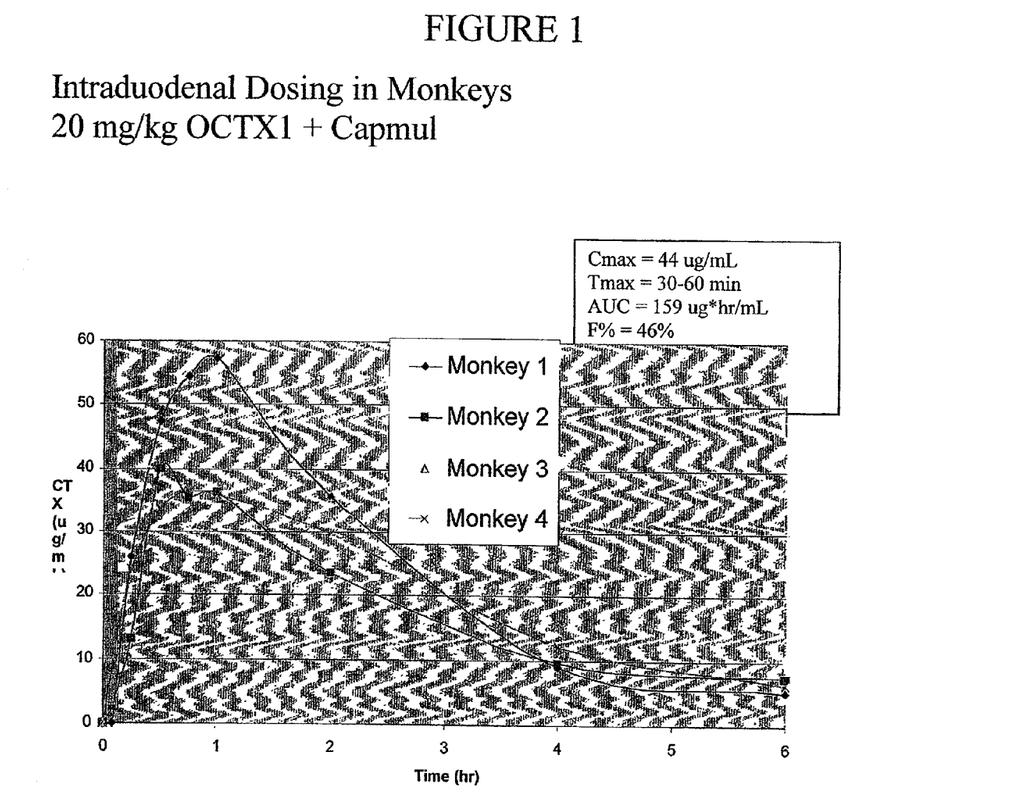
FIG. 1 is a graphical representation of the results of administering OCTX1 and capmul to monkeys.
Figure 2:
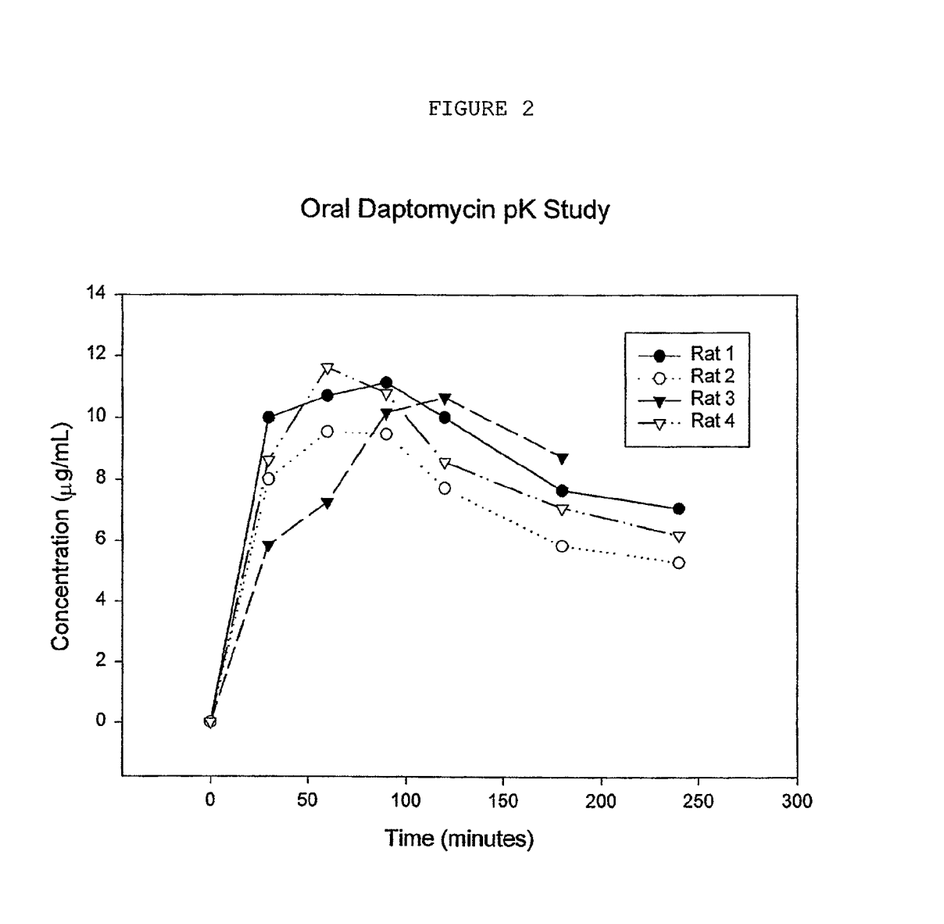
FIG. 2 is a graphical representation of the results of administering a daptomycin complex according to the invention.
Figure 3:
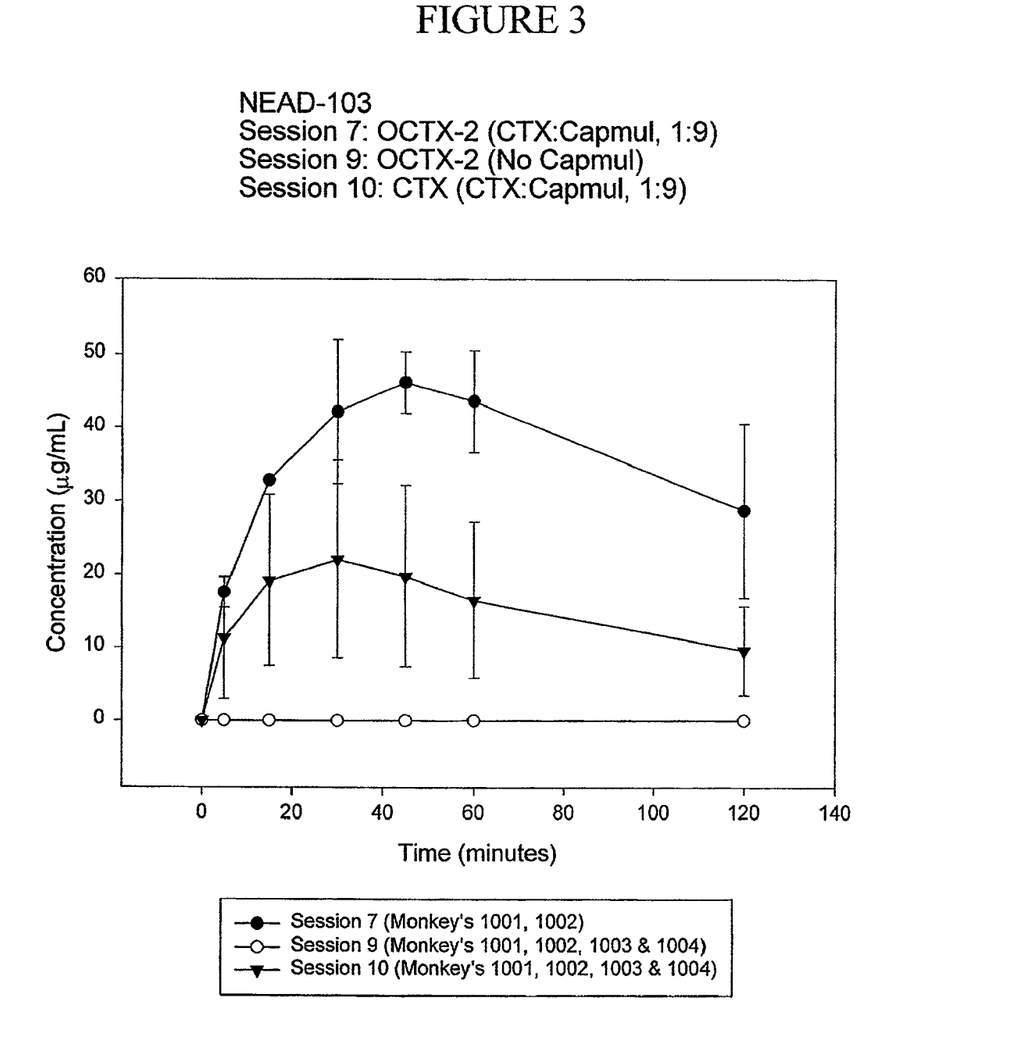
FIG. 3 is a graphical comparison of formulations having ceftriaxone+capmul, OCTX2+an absorption enhancer, and OCTX2 without capmul.
Figure 4:
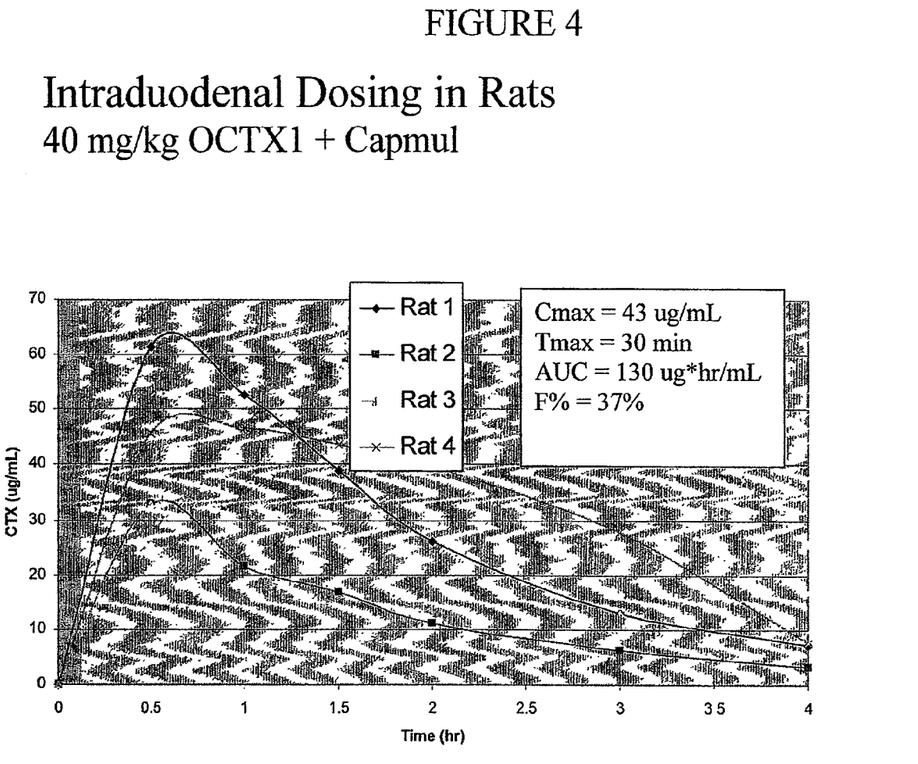
FIG. 4 is a graphical representation of the results of administering OCTX1 and capmul to rats.

About 400 mg of carrageenan was added to 80 ml of an aqueous solution containing 1.0 g (0.62 mmole) of Daptomycin. The solution was then mixed by magnetic stirrer at room temperature until the carrageenan was essentially fully swollen, forming a daptomycin-carrageenan hydrogel. Next, an aqueous solution containing calcium ions was prepared by dissolving 18.23 mg (0.125 mmole) of calcium chloride in 20 ml of water. The entire aqueous solution was then dropped into the daptomycin-carrageenan hydrogel or suspension. The complex was then mixed by a magnetic stirrer at room temperature for 2 hours. This resulted in the formation of a daptomycin-Ca-carrageenan gel complex. The daptomycin-Ca-carrageenan gel was then freeze-dried while in the swollen state. See FIG. 2.

Results:

| Time point | rat 1 | rat 2 | rat 3 | rat 4 |
|---|---|---|---|---|
| 0 | 0.00 | 0.00 | 0.00 | 0.00 |
| 30 | 10.0 | 8.01 | 5.86 | 8.63 |
| 60 | 10.70 | 9.54 | 7.27 | 11.62 |
| 90 | 11.13 | 9.47 | 10.17 | 10.79 |
| 120 | 10.01 | 7.74 | 10.66 | 8.58 |
| 180 | 7.68 | 5.85 | 8.76 | 7.10 |
| 240 | 7.09 | 5.31 | no sample | 6.20 |

Example 15

Preparation of Aztreonam-Arg-CG

About 400 mg of carrageenan was added to 80 ml of an aqueous solution at approximately 50° C. The solution was then mixed by magnetic stirrer at room temperature until the carrageenan was essentially fully swollen. Next, an aqueous solution containing arginine was prepared by dissolving 240 mg (0.33 mole) of arginine in 10 ml of water. An aqueous solution of aztreonam was prepared by dissolving 120 mg aztreonam in 10 ml of water. The entire volume of aztreonam and $CaCl_2$ solutions were simultaneously added dropwise to the hydrogel CG solution. The dispersion was centrifuged and the supernatant removed for subsequent lyophilization to dryness. The resulting composition contains 7.57 mg of aztreonam/10 mg of composition, and can be milled to yield a fine powder.

Example 16

Preparation of Pipericillin-CG-CA

About 400 mg of carrageenan was added to 80 ml of an aqueous solution at approximately 50° C. The solution was then mixed by magnetic stirrer at room temperature until the carrageenan was essentially fully swollen. Next, an aqueous solution containing $Ca^{2+}$ ions was prepared by dissolving 54.5 mg (0.37 mmole) of calcium chloride in 10 ml of water. An aqueous solution of pipericillin was prepared by dissolving 1 mg (1.85 mmole) pipericillin in 10 ml of water. The entire volume of pipericillin and $CaCl_2$ solutions were simultaneously added dropwise to the hydrogel CG solution. The dispersion was centrifuged and the supernatant removed for subsequent lyophilization to dryness. 10 mg of the final composition contained 6.88 mg pipericillin.

Example 17

Preparation of a Vancomycin-CG-CA Complex

About 400 mg of carrageenan was added to 80 ml of an aqueous solution at approximately 50° C. The solution was then mixed by magnetic stirrer at room temperature until the carrageenan was essentially fully swollen. Next, an aqueous solution containing $Ca^{2+}$ ions was prepared by dissolving 20 mg (0.0.14 mmole) of calcium chloride in 10 ml of water. An aqueous solution of vancomycin was prepared by dissolving 1 g (0.67 mmole) vancomycin in 10 ml of water. The entire volume of vancomycin and $CaCl_2$ solutions were simultaneously added dropwise to the hydrogel CG solution. The dispersion was centrifuged and the supernatant removed for subsequent lyophilization to dryness. 10 mg of the resulting composition comprises 3.62 mg of vancomycin.

Example 18

Preparation of an Amikacin-CG-CA Complex

About 400 mg of carrageenan was added to 80 ml of an aqueous solution at approximately 50° C. The solution was then mixed by magnetic stirrer at room temperature until the carrageenan was essentially fully swollen. Next, an aqueous solution containing $Ca^{2+}$ ions was prepared by dissolving 50 g of calcium chloride in 10 ml of water. An aqueous solution of amikacin was prepared by dissolving 1 g amikacin in 10 ml of water. The entire volume of amikacin and $CaCl_2$ solutions were simulataneously added dropwise to the hydrogel CG solution. The dispersion was centrifuged and the supernatant removed for subsequent lyophilization to dryness. The resulting composition comprises 6.9 mg of amikacin/10 mg formulation.

Example 19

Preparation of Amoxacillin-CG-Ca

About 400 mg of carrageenan was added to 80 ml of an aqueous solution at approximately 50° C. The solution was then mixed by magnetic stirrer at room temperature until the carrageenan was essentially fully swollen. Next, an aqueous solution containing $Ca^{2+}$ ions was prepared by dissolving 69.98 mg (0.48 mmole) of calcium chloride in 10 ml of water. An aqueous solution of amoxicillin was prepared by dissolving 0.25 mg (0.6 mmole) amoxicillin in 10 ml of water. The entire volume of amoxicillin and $CaCl_2$ solutions were simultaneously added dropwise to the hydrogel CG solution. The dispersion was centrifuged and the supernatant removed for subsequent lyophilization to dryness. 10 mg of the final composition contained 3.47 mg amoxicillin.

While this invention has been particularly shown and described with references to a few preferred embodiments, it will be understood by those skilled in the art that various changes in form and details may be made therein without departing from the spirit and scope of the invention as defined by the appended claims.

What is claimed is:
1. A method for increasing the oral bioavailability of a cephalosporin in an animal comprising administering to an animal in need thereof a pharmaceutical composition comprising:
   a) a biopolymer including carrageenan having a calcium content of less than about 0.4% by weight;
   b) a cephalosporin; and
   c) an absorption enhancer selected from the group consisting of a monoglyceride of a $C_{12}$-$C_{18}$ fatty acid, a diglyceride of a $C_6$-$C_{18}$ fatty acid, a triglyceride of a $C_{12}$-$C_{18}$ fatty acid, gelucire and mixtures thereof.

* * * * *